United States Patent
Shanbhag et al.

(10) Patent No.: US 12,048,521 B2
(45) Date of Patent: Jul. 30, 2024

(54) SYSTEM AND METHOD FOR IMPROVED METAL DETECTION IN MAGNETIC RESONANCE IMAGING

(71) Applicant: GE Precision Healthcare LLC, Wauwatosa, WI (US)

(72) Inventors: Dattesh Dayanand Shanbhag, Bangalore (IN); Chitresh Bhushan, Glenville, NY (US); Deepa Anand, Bangalore (IN); Kavitha Manickam, Pewaukee, WI (US); Dawei Gui, Sussex, WI (US); Radhika Madhavan, Latham, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 3 days.

(21) Appl. No.: 17/973,855

(22) Filed: Oct. 26, 2022

(65) Prior Publication Data
US 2024/0138697 A1 May 2, 2024

(51) Int. Cl.
*A61B 5/055* (2006.01)
*G01R 33/20* (2006.01)
*G01R 33/56* (2006.01)

(52) U.S. Cl.
CPC .............. *A61B 5/055* (2013.01); *G01R 33/20* (2013.01); *G01R 33/5608* (2013.01)

(58) Field of Classification Search
CPC ...... G01R 33/20; G01R 33/5608; A61B 5/055
See application file for complete search history.

(56) References Cited

U.S. PATENT DOCUMENTS

| | | | |
|---|---|---|---|
| 9,678,190 B2 | 6/2017 | Koch | |
| 10,436,858 B2 | 10/2019 | Shanbhag | |
| 10,478,090 B2 * | 11/2019 | Koch | A61B 5/7267 |
| 10,543,361 B2 | 1/2020 | Ramani | |
| 10,638,949 B2 | 5/2020 | Koch | |
| 11,790,525 B2 * | 10/2023 | Siewerdsen | G06T 11/006 |
| | | | 382/131 |
| 2021/0080531 A1 * | 3/2021 | Gui | A61B 5/7264 |

FOREIGN PATENT DOCUMENTS

| CN | 112748382 A | 5/2021 |
|---|---|---|
| CN | 112763958 B | 6/2022 |

OTHER PUBLICATIONS

Kwon et al. "Unsupervised learning of a deep neural network for metal artifact correction using dual-polarity readout gradients", Magn Reson Med. 2020; 83: 124-138, 15 pages.

* cited by examiner

*Primary Examiner* — Gregory H Curran

(57) ABSTRACT

A method for generating an image of a subject with a magnetic resonance imaging (MRI) system is presented. The method includes first performing a localizer scan of the subject to acquire localizer scan data. A machine learning (ML) module is then used to detect the presence of metal regions in the localizer scan data based on magnitude and phase information of the localizer scan data. Based on the detected metal regions in the localizer scan data, the MRI workflow is adjusted for diagnostic scan of the subject. The image of the subject is then generated using the adjusted workflow.

20 Claims, 5 Drawing Sheets

SYSTEM AND METHOD FOR IMPROVED METAL DETECTION IN MAGNETIC RESONANCE IMAGING

BACKGROUND

The field of the disclosure relates generally to medical imaging systems and methods, and more particularly, to a technique of detecting a metal region in magnetic resonance imaging (MRI) data using machine learning-based applications.

As a medical imaging modality, Magnetic resonance imaging (MRI), can obtain images of the human body without using X-rays or other ionizing radiation. MRI uses a magnet having a strong magnetic field to generate a static magnetic field B0. When a part of the human body to be imaged is positioned in the static magnetic field B0, nuclear spin associated with hydrogen nuclei in human tissue is polarized, so that the tissue of the to-be-imaged part generates a longitudinal magnetization vector at a macroscopic level. After a radio-frequency field B1 intersecting the direction of the static magnetic field B0 is applied, the direction of rotation of protons changes so that the tissue of the to-be-imaged part generates a transverse magnetization vector at a macroscopic level. After the radio-frequency field B1 is removed, the transverse magnetization vector decays in a spiral manner until it is restored to zero. A free induction decay signal is generated during decay. The free induction decay signal can be acquired as a magnetic resonance signal, and a tissue image of the to-be-imaged part can be reconstructed based on the acquired signal.

Since MRI uses a magnet having a strong magnetic field to generate a static magnetic field B0, metal implants inside the body of the patient may cause distortions in patient images. Many methods have been developed in recent times to detect metal regions in the body of the patient. However, it is still challenging to acquire good quality MR images in presence of metal regions in the body. Especially in the Artificial Intelligence (AI) based automated MRI, it is even more important to detect the metal regions accurately.

Therefore, there is a need for an improved magnetic resonance imaging system and method.

BRIEF DESCRIPTION

In accordance with an embodiment of the present technique, a method for generating an image of a subject with a magnetic resonance imaging (MRI) system is presented. The method includes performing a localizer scan of the subject using the MRI system to acquire localizer scan data and using a machine learning (ML) module to detect the presence of metal regions in the localizer scan data based on magnitude and phase information of the localizer scan data. The method further includes adjusting a workflow of the MRI system based on the detected metal regions in the localizer scan data for a diagnostic scan of the subject and generating the image of the subject using the adjusted workflow.

In accordance with another embodiment of the present technique, a magnetic resonance imaging (MRI) system is presented. The MRI system includes a magnet configured to generate a polarizing magnetic field about at least a portion of an object arranged in the MRI system. A gradient coil assembly including a readout gradient coil, a phase gradient coil, a slice selection gradient coil configured to apply at least one gradient field to the polarizing magnetic field is also provided in the MRI system. The MRI system also includes a radio frequency (RF) system configured to apply an RF field to the object and to receive magnetic resonance signals from the object. A processing system is also provided in the MRI system. The processing system is programmed to perform a localizer scan of the subject using the MRI system to acquire localizer scan data and detect the presence of metal regions in the localizer scan data using a machine learning (ML) module based on magnitude and phase information of the localizer scan data. The processing system is also programmed to adjust a workflow of the MRI system based on the detected metal regions in the localizer scan data for a diagnostic scan of the subject and generate the image of the object using the adjusted workflow.

DRAWINGS

These and other features, aspects, and advantages of the present invention will become better understood when the following detailed description is read with reference to the accompanying drawings in which like characters represent like parts throughout the drawings, wherein.

Figure 7:
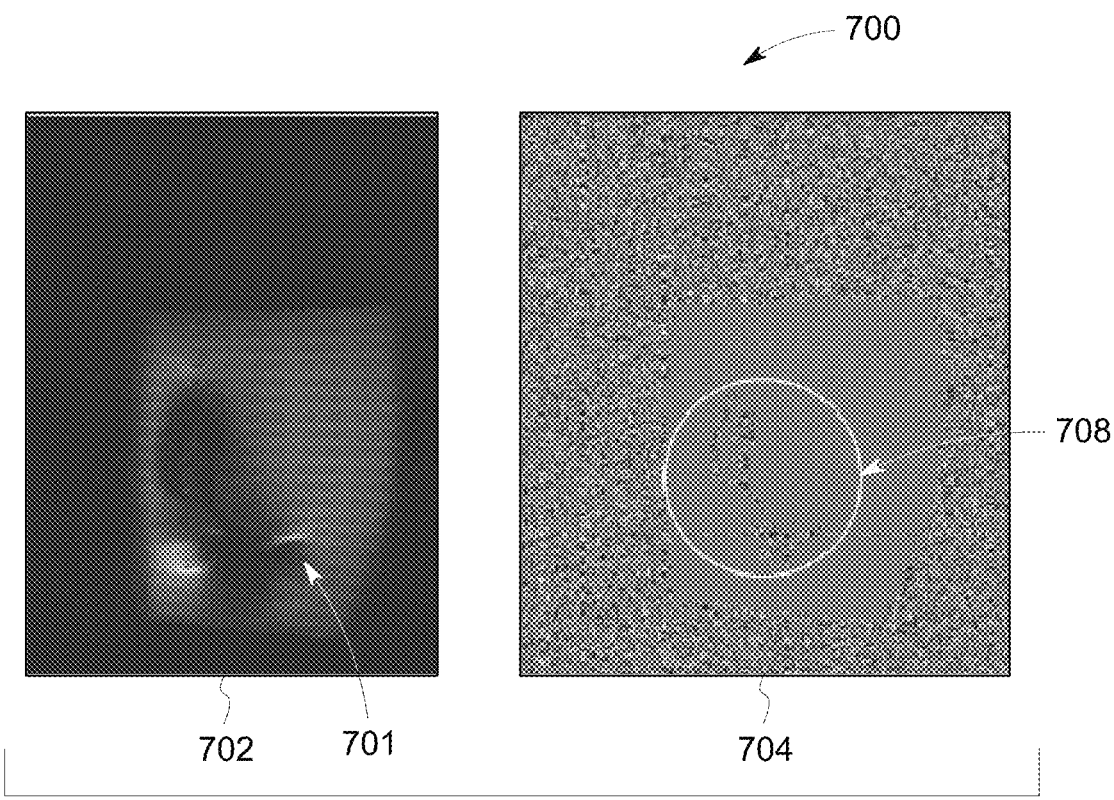
Figure 8:
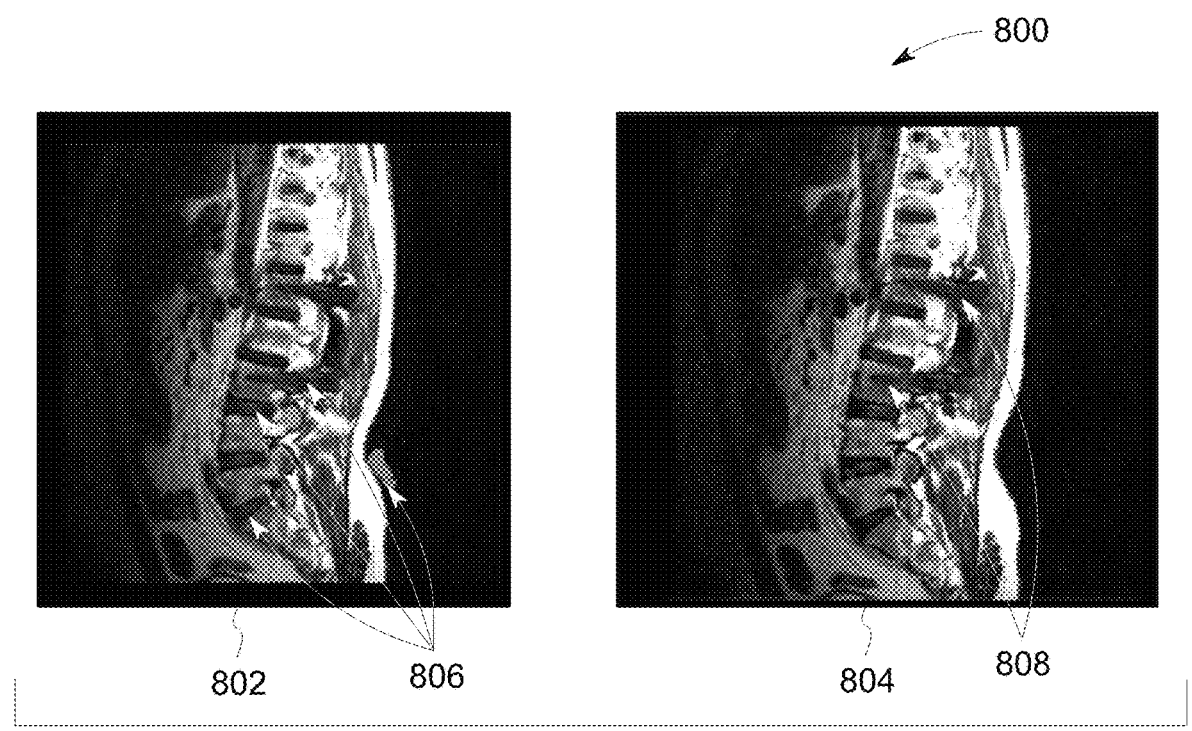

FIG. 7 is a schematic diagram showing one example of effects of metal implants in magnitude and phase images in accordance with an embodiment of the present technique; and FIG. 8 is a schematic diagram comparing metal detection results in a conventional method utilizing only magnitude information and the present technique utilizing both phase and magnitude information in accordance with an embodiment of the present technique.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. Furthermore, the terms "circuit" and "circuitry" and "controller" may include either a single component or a plurality of components, which are either active and/or passive and are connected or otherwise coupled together to provide the described function.

The term "a machine learning module" is used herein to refer to an artificial intelligence (AI)/machine learning (ML) model configured to perform a signal processing or analysis task on quasi-stationary signals. The signal processing or analysis task can vary. In various examples, the signal processing or analysis task can include, (but is not limited to): a segmentation task, an image reconstruction task, an object recognition task, a motion detection task, an optical flow task, an attention region identification task, an object labeling task and the like. The machine learning module can employ various types of AI/ML algorithms, including (but not limited to): deep learning models, neural network models, deep neural network models (DNNs), convolutional neural network models (CNNs), and the like.

The presented technique includes systems and methods of detecting metal regions in the subject image using machine learning model. As used herein, a subject is a human (or patient), an animal, or a phantom. The machine learning model uses both the magnitude and phase information of the received MR signals to detect the metal region. The MRI workflow is then adjusted based on the detected metal regions. In general, subject conditions such as metal implants cause artifacts (i.e., visual anomalies in the medical images that are not present in the subject) in MR images. The adjusted MRI workflow reduces or eliminates these metal artifacts in the MR images. Method aspects will be in part apparent and in part explicitly discussed in the following description.

Figure 1:
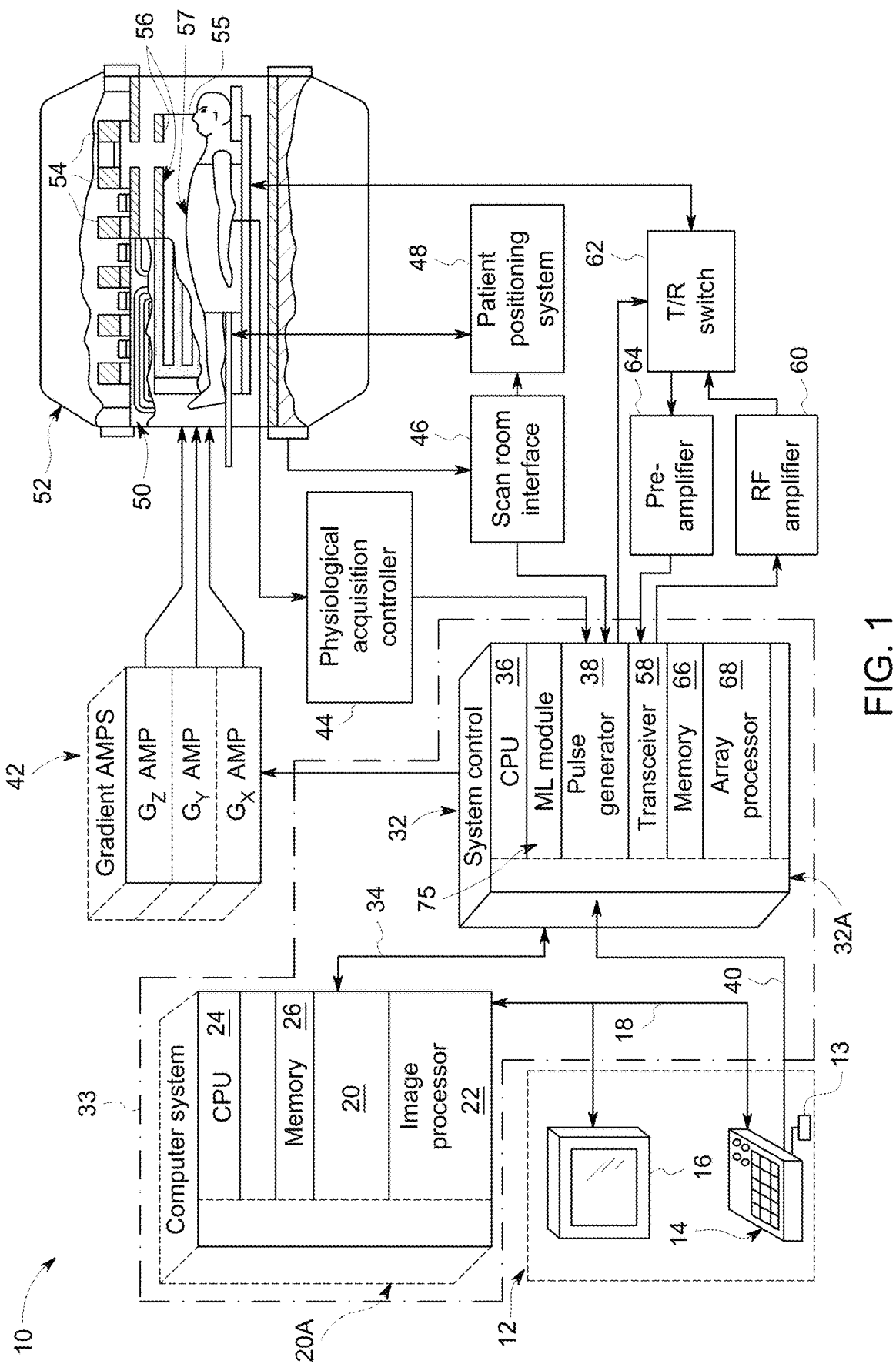
FIG. 1 is a schematic diagram of an exemplary magnetic resonance imaging (MRI) system in accordance with an embodiment of the present technique.

Embodiments of the present disclosure will now be described, by way of an example, with reference to the figures, in which FIG. 1 is a schematic diagram of a magnetic resonance imaging (MRI) system 10. Operation of the system 10 may be controlled from an operator console 12, which includes an input device 13, a control panel 14, and a display screen 16. The input device 13 may be a mouse, joystick, keyboard, track ball, touch activated screen, light wand, voice control, and/or other input device. The input device 13 may be used for interactive geometry prescription. The console 12 communicates through a link 18 with a computer system 20 that enables an operator to control the production and display of images on the display screen 16. The link 18 may be a wireless or wired connection. The computer system 20 may include modules that communicate with each other through a backplane 20a. The modules of the computer system 20 may include an image processor module 22, a central processing unit (CPU) module 24, and a memory module 26 that may include a frame buffer for storing image data arrays, for example. The computer system 20 may be linked to archival media devices, permanent or back-up memory storage or a network for storage of image data and programs and communicates with MRI system control 32 through a high-speed signal link 34. The MRI system control 32 may be separate from or integral with the computer system 20. The computer system 20 and the MRI system control 32 collectively form an "MRI controller" 33 or "controller".

In the exemplary embodiment, the MRI system control 32 includes modules connected by a backplane 32a. These modules include a CPU module 36, a machine learning module 75 as well as a pulse generator module 38. The CPU module 36 connects to the operator console 12 through a data link 40. The MRI system control 32 receives commands from the operator through the data link 40 to indicate the scan sequence that is to be performed. The CPU module 36 operates the system components to carry out the desired scan sequence and produces data which indicates the timing, strength and shape of the RF pulses produced, and the timing and length of the data acquisition window. The CPU module 36 connects to components that are operated by the MRI controller 32, including the pulse generator module 38 which controls a gradient amplifier 42, a physiological acquisition controller (PAC) 44, and a scan room interface circuit 46.

In one example, the CPU module 36 receives patient data from the physiological acquisition controller 44, which receives signals from sensors connected to the object, such as ECG signals received from electrodes attached to the patient. As used herein, an object is a human (or patient), an animal, or a phantom. The CPU module 36 receives, via the scan room interface circuit 46, signals from the sensors associated with the condition of the patient and the magnet system. The scan room interface circuit 46 also enables the MRI controller 33 to command a patient positioning system 48 to move the patient to a desired position for scanning.

A whole-body RF coil 56 is used for transmitting the waveform towards subject anatomy. The whole body-RF coil 56 may be a body coil. An RF coil may also be a local coil that may be placed in more proximity to the subject anatomy than a body coil. The RF coil 56 may also be a surface coil. RF coils containing RF receiver channels may be used for receiving the signals from the subject anatomy. Typical surface coil would have eight receiving channels; however, different number of channels are possible. Using the combination of both a body coil 56 and a surface coil is known to provide better image quality.

The MR signals produced from excitation of the target are digitized by the transceiver module 58. The MR system control 32 then processes the digitized signals by Fourier transform to produce k-space data, which is transferred to a memory module 66, or other computer readable media, via the MRI system control 32. "Computer readable media" may include, for example, structures configured so that electrical, optical, or magnetic states may be fixed in a manner perceptible and reproducible by a conventional computer (e.g., text or images printed to paper or displayed on a screen, optical discs, or other optical storage media, "flash" memory, EEPROM, SDRAM, or other electrical storage media; floppy or other magnetic discs, magnetic tape, or other magnetic storage media).

A scan is complete when an array of raw k-space data has been acquired in the computer readable media 66. This raw k-space data is rearranged into separate k-space data arrays for each image to be reconstructed, and each of these k-space data arrays is input to an array processor 68, which operates to reconstruct the data into an array of image data, using a reconstruction algorithm such as a Fourier transform. When the full k-space data is obtained, it represents entire volume of the subject body and the k-space so obtained may be referred as the reference k-space. Similarly, when only the partial k-space data is obtained, the image may be referred as the partial k-space. This image data is conveyed through the data link 34 to the computer system 20 and stored in memory. In response to the commands received from the operator console 12, this image data may be archived in a long-term storage or may be further processed by the image processor 22 and conveyed to the operator console 12 and presented on the display 16.

MR signals are represented by complex numbers, where each location at the k-space is represented by a complex number, with I and Q quadrature MR signals being the real and imaginary components. Complex MR images may be reconstructed based on I and Q quadrature MR signals, using processes such as Fourier transform of the k-space MR data. Complex MR images are MR images with each pixel represented by a complex number, which also has a real component and an imaginary component. The magnitude M of the received MR signal may be determined as the square root of the sum of the squares of the I and Q quadrature components of the received MR signal as in Eq. (3) below:

$$M = \sqrt{I^2 + Q^2} \quad (1)$$

and the phase $\phi$ of the received MR signal may also be determined as in eq. (2) below:

$$\phi = \tan^{-1}\left(\frac{Q}{I}\right) \quad (2)$$

As discussed earlier, detection of metal regions is very important for the MRI system. Thus, a localizer scan (also called as a scout scan or survey scan) of a subject may be acquired before acquiring the diagnostic scan. The localizer scan acquires localizer scan data such as low-resolution surface coil and body coil images also called as localizer images. In one embodiment, a machine learning (ML) module 75 receives phase information and magnitude information of a localizer scan data. The phase information and the magnitude information may be reconstructed phase and magnitude images respectively. The ML module then determines metal regions in the localizer scan data. A workflow of the MR system may be adjusted using the determined metal regions. Once the workflow is adjusted, the adjusted workflow is used to acquire the diagnostic scan of the subject to generate the image of the subject.

Figure 2:
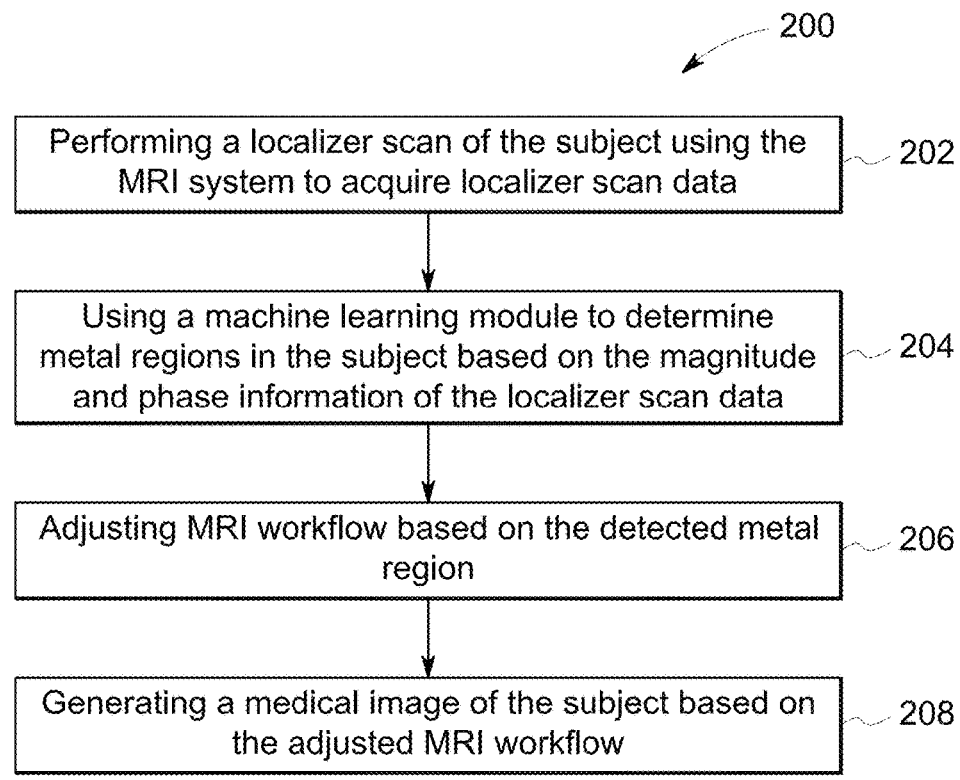
FIG. 2 is a flowchart depicting a method for imaging a subject in accordance with an embodiment of the present technique.

FIG. 2 is a flowchart of a method 200 for generating the MR image of an object with the MRI system 10 according to an embodiment of the present technique. The method 200 may be implemented on the MRI controller 33 in coordination with other components of the MRI system. At step 202, the method includes performing a localizer scan of the object to acquire localizer scan data. The localizer scan may include a low-resolution scan (as compared to the diagnostic scan) of the field of view (FOV) of the MRI system where the acquired image is used to reconstruct an MR image of the FOV to confirm that the desired anatomy is within the FOV.

Once the localizer scan is performed, a trained machine learning (ML) module is used in step 204 to determine metal regions in the localizer scan data (i.e., FOV) based on the magnitude and the phase information of the localizer scan data. In one embodiment, the magnitude and phase information may include a localizer magnitude image and a localizer phase image. The ML module may include a deep learning (DL) network that learns from training data. In some embodiments, training data includes a plurality of complex MR images comprising the magnitude and phase images and corresponding metal artifact regions in the same anatomical region. In one embodiment, determining metal regions may include segmenting metal regions (i.e., generating segmentation masks) from the localizer scan data.

In general, if magnitude information of the localizer scan data is used to determine metal region, then there can be many false negatives and false positives. For example, metal parts create dark signals in magnitude images but tissue in the anatomical region can also create dark signals in the magnitude image. Therefore, there may be a lot of false positives. However, a phase image is very reliable even in soft tissue. The phase image is generally slowly varying/constant/flat but where there is no MR signal (such as in a metal region), the phase image is random. FIG. 7 shows an example of both a metal image 702 and a phase image 704 obtained for an anatomy having metal implants. As can be seen both magnitude image 702 and phase image 704 show metal regions 701 and 708 respectively. However, the metal region 701 in magnitude image 702 is not as accurate as the metal region 708 in phase image 704. Thus, by using both phase image and the magnitude image, false positives can be reduced significantly. Moreover, in the present technique, it was determined that by using both phase image and the metal image to determine the metal regions using the ML module has very few false negatives as compared to determining the metal regions using only the magnitude image.

At step 206, the method includes adjusting the MRI workflow for diagnostic scan of the subjected based on the detected metal region in step 204. In general, in the MRI scan, the MR data is acquired for a plurality of slice images (i.e., slices). Many a times these slices are parallel to each other but at times (for example, for spine MRI scan) these slices may oriented at different angles. The location and orientation of slices (e.g., slice angle for each slice), as well as the number of slices, is specified by the operator and accordingly the MR data is acquired. In one embodiment of the present technique, adjusting the MRI workflow may include acquiring MRI slices using a block approach. In the block approach, the slices that are affected by the metal are grouped into a block and no separate slice angle is determined for the slices in that block. MR data for the MR slices in the block is then acquired using the slice angle for the slices before or after the metal region. In one embodiment, this process can also be automated i.e., a processor may generate the block of MRI slices automatically when the metal region is detected. In another embodiment where a quantitative imaging is being performed, a signal may be generated to avoid the quantification in the detected metal region of the anatomy images.

Finally, at step 208, the image of the subject is generated using the adjusted workflow. In one embodiment, generating the image of the subject includes reconstructing the MRI image based on the MRI data acquired with the adjusted workflow in step 206. In one embodiment, a reconstruction algorithm such as a Fourier transform may be used to reconstruct the MRI image.

Figure 3:
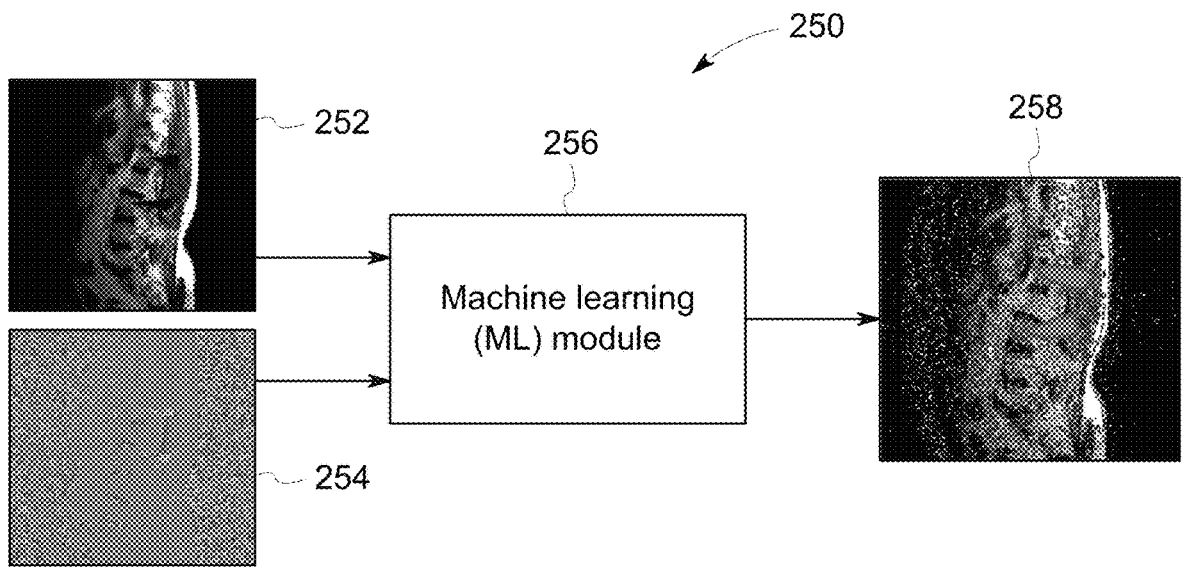
FIG. 3 is a schematic diagram of a system of detecting metal regions in a medical image in accordance with an embodiment of the present technique.

FIG. 3 is a system 250 of detecting metal regions in a medical image in accordance with an embodiment of the present technique. The system 250 includes a trained machine learning (ML) module 256. The ML module may include a deep learning (DL) network and other processing modules to clean up the image output of the DL module. In one embodiment, the processing module may include a mapping module to map the output of the DL network with the phase image. In another embodiment, the processing modules may include image filters to filter out any phase consistency in the detected metal region. In yet another embodiment, the processing modules may include a mask generation module to label the metal regions. As discussed earlier, the DL module in the ML module 256 is trained in advance with training images that includes phase and magnitude MR images and relevant ground truth metal masks.

As can be seen from FIG. 3, during the operation, a localizer magnitude image 252 and a localizer phase image 254 is provided as two inputs to the ML module 256. Both the localizer magnitude image 252 and localizer phase image 254 are low resolution images generated during the localizer scan of the subject. The localizer scan is performed before the diagnostic scan of the subject. The output of the ML module 256 is an image 258 with detected (i.e., labeled) metal regions. It can be seen that the metal regions are clearly defined in image 258 as compared to the localizer magnitude image 252.

Figure 4:
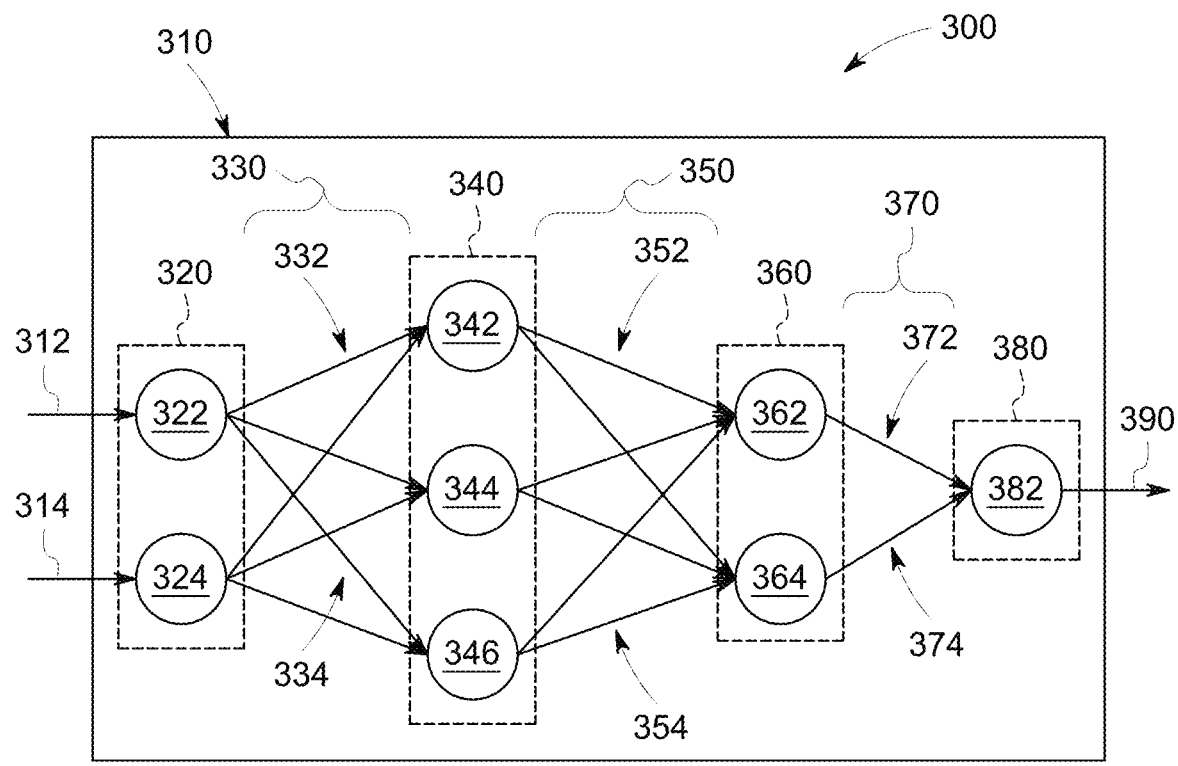
FIG. 4 is a schematic diagram of an example machine learning (ML) module that may be used in the system of FIG. 3 in accordance with an embodiment of the present technique.

FIG. 4 is an example (ML) module 300 that may be used in the system of FIG. 3 in accordance with an embodiment of the present technique. The ML module 300 is essentially a deep learning (DL) network 310. The example DL network model 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314 from the input layer 320 to the output layer 380 and to an output 390. The inputs 312, 314 may be localizer magnitude and phase images and output 390 may be an image with metal masks.

The layer 320 is an input layer that, in the example of FIG. 4, includes a plurality of nodes 322, 324. The layers 340 and 360 are hidden layers and include, in the example of FIG. 4, nodes 342, 344, 346, 362, 364, 366. The DL network model 300 may include more or less hidden layers 340 and 360 than shown. The layer 380 is an output layer and includes, in the example of FIG. 4 a node 382 with an output 390. Each input 312-314 corresponds to a node 322-324 of the input layer 320, and each node 322-324 of the input layer 320 has a connection 330 to each node 342-346 of the hidden layer 340. Each node 342-346 of the hidden layer 340 has a connection 350 to each node 362-364 of the hidden layer 360. Each node 362-364 of the hidden layer 360 has a connection 370 to the output layer 380. The output layer 380 has an output 390 to provide an output from the example DL network model 300.

Of connections 330, 350, and 370 certain example connections 332, 352, 372 may be given added weight while other example connections 334, 354, 374 may be given less weight in the DL network model 300. Input nodes 322-324 are activated through receipt of input data via inputs 312-314, for example. Nodes 342-346 and 362-364 of hidden layers 340 and 360 are activated through the forward flow of data through the network model 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the DL network model 300.

Figure 5:
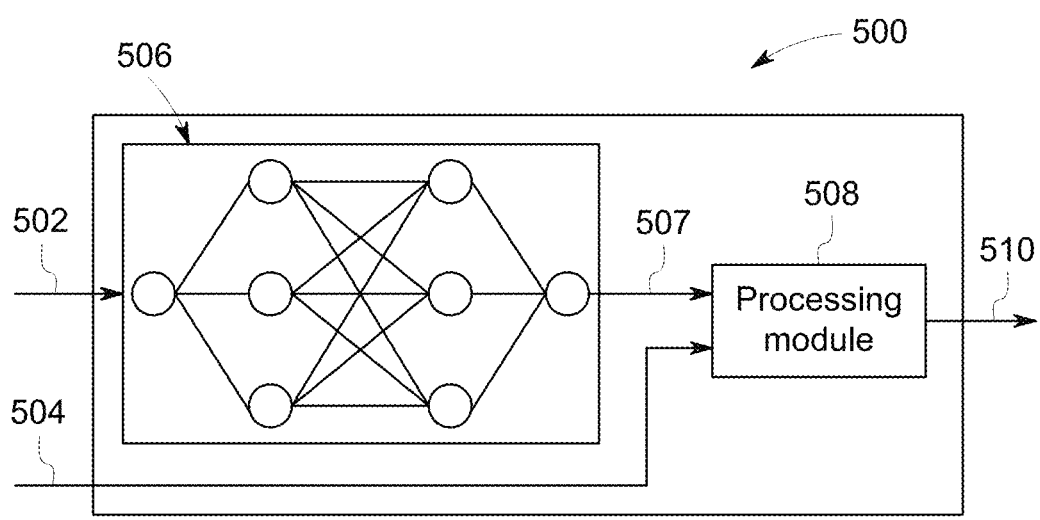
FIG. 5 is a schematic diagram of another ML module that may be used in the system of FIG. 3 in accordance with an embodiment of the present technique.

FIG. 5 is another ML module 500 that may be used in the system of FIG. 3 in accordance with an embodiment of the present technique. The ML module 500 includes a DL network 506 and a processing module 508. The DL network 506 receives a localizer magnitude image 502 as an input but not a localizer phase image 504 unlike DL network 300 of FIG. 4. The output signal 507 of the DL network 506 may include metal masks provided on top of the magnitude image. However, the output signal 507 is then further mapped by the processing module 508 with the localizer phase image 504 to generate an image 510 with refined metal masks. In general, the phase image is very reliable in soft tissue of the patient. Generally, the phase is mostly constant or slowly varying but where there is metal region i.e., where there is no MR signal (such as in metal region), the phase image is random in those areas. Thus, mapping the output of the DL network with the phase image provides a better estimate of the metal regions in the localizer scan data.

Figure 6:
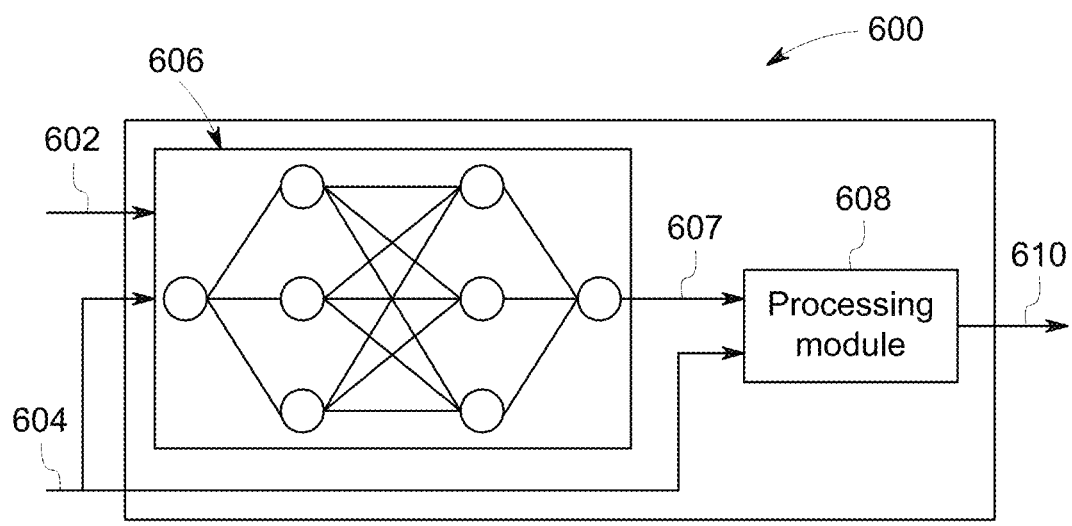
FIG. 6 is a schematic diagram of yet another ML module that may be used in the system of FIG. 3 in accordance with an embodiment of the present technique.

FIG. 6 is another ML module 600 that may be used in the system of FIG. 3 in accordance with an embodiment of the present technique. The ML module 600 includes a DL network 606 and a processing module 608. The DL network 606 receives both a magnitude image 602 and a phase image 604 as inputs and generates an output 607 which may include an image with metal masks. The output 607 of the DL network 606 i.e., the masks are further refined by checking for the phase consistency in detected metal regions using the phase image 604 and then filtering out the inconsistencies accordingly. In other words, the output 607 of the DL network 606 is also an image with metal masks, however, these masks are further refined by the processing module 608 by comparing them with the actual phase image 604. In one embodiment, the refinement of the masks 607 can be done on a pixel by pixel basis or a component by component basis.

FIG. 8 is a schematic diagram 800 comparing metal detection results of conventional machine learning method and the present technique. Specifically, in FIG. 8, image 802 shows metal detection results of the conventional method where only magnitude information is used. Further image 804 shows metal detection results of the present technique having a ML module that uses both metal and phase information from the localizer scan. In the image 802, masks 806 show metal regions whereas in the image 804, masks 808 shows metal regions in a spine. It can be seen that in the conventional method i.e., image 802, there are more false positives as compared to the false positives of present technique result i.e., image 804. In other words, image 802 shows more metal regions than there actually are as compared to the metal regions in image 804

One of the advantages of the present technique is that it allows automatic MR scan plan prescription to be enabled even in patients with implants. Moreover, for MR technologist, the present technique facilitates easy acquisition of various landmark data in the patient anatomy even in presence of implant or provides a guided work to handle MRI data scanning in regions of metal implants.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for generating an image of a subject with a magnetic resonance imaging (MRI) system, the method comprising:
  performing a localizer scan of the subject using the MRI system to acquire localizer scan data;

using a machine learning (ML) module to detect the presence of metal regions in the localizer scan data based on magnitude and phase information of the localizer scan data;

adjusting a workflow of the MRI system based on the detected metal regions in the localizer scan data for a diagnostic scan of the subject;

generating the image of the subject using the adjusted workflow.

2. The method of claim 1, wherein the machine learning module includes a deep learning (DL) network.

3. The method of claim 2, wherein the magnitude information and the phase information of the localizer scan data includes a localizer magnitude image and a localizer phase image respectively.

4. The method of claim 3, wherein the deep learning (DL) network receives the localizer magnitude image and the localizer phase image as inputs and the DL network outputs metal masks.

5. The method of claim 3, wherein the metal masks are further mapped with the localizer phase image using a processing module to further refine the metal masks.

6. The method of claim 5, wherein refining the metal masks includes mapping the localizer phase image with the metal masks on a pixel by pixel basis or a component by component basis.

7. The method of claim 3, wherein the (DL) network receives the localizer magnitude image as input to generate metal masks and the metal masks are further mapped with the localizer phase image using a processing module.

8. The method of claim 1, wherein adjusting the workflow of the MRI system includes grouping MR slices in the detected metal region into a block.

9. The method of claim 8, wherein adjusting the workflow of the MRI system includes acquiring MR data for the MR slices in the block using a slice angle for the MR slices before or after the metal region.

10. The method of claim 1, wherein generating the image of the subject includes reconstructing a MR image based on the MR data acquired with the adjusted workflow.

11. A magnetic resonance imaging (MRI) system, comprising:
 a magnet configured to generate a polarizing magnetic field about at least a portion of an object arranged in the MRI system;
 a gradient coil assembly including a readout gradient coil, a phase gradient coil, a slice selection gradient coil configured to apply at least one gradient field to the polarizing magnetic field;
 a radio frequency (RF) system configured to apply an RF field to the object and to receive magnetic resonance signals from the object;
 a processing system programmed to:
  perform a localizer scan of the subject using the MRI system to acquire localizer scan data;
  detect the presence of metal regions in the localizer scan data using a machine learning (ML) module based on magnitude and phase information of the localizer scan data;
  adjust a workflow of the MRI system based on the detected metal regions in the localizer scan data for a diagnostic scan of the subject; and
  generate the image of the object using the adjusted workflow.

12. The MRI system of claim 11, wherein the machine learning module includes a deep learning (DL) network.

13. The MRI system of claim 12, wherein the magnitude information and the phase information of the localizer scan data includes a localizer magnitude image and a localizer phase image respectively.

14. The MRI system of claim 13, wherein the deep learning (DL) network receives the localizer magnitude image and the localizer phase image as inputs and the DL network outputs metal masks.

15. The MRI system of claim 13, wherein the metal masks are further mapped with the localizer phase image using a processing module to further refine the metal masks.

16. The MRI system of claim 15, wherein the processing system is programmed to refine the metal masks with the localizer phase image on a pixel by pixel basis or a component by component basis.

17. The MRI system of claim 13, wherein the (DL) network receives the localizer magnitude image as input to generate metal masks and the metal masks are further mapped with the localizer phase image using a processing module.

18. The MRI system of claim 13, wherein the processing system is programed to adjust the workflow of the MRI system by grouping MR slices in the detected metal region into a block.

19. The MRI system of claim 18, wherein the processing system is programed to adjust the workflow of the MRI system by acquiring MR data for the MR slices in the block using a slice angle for the MR slices before or after the metal region.

20. The MRI system of claim 11, wherein the processing system is programmed to generate the image of the subject by reconstructing a MR image based on the MR data acquired with the adjusted workflow.

* * * * *